US011464772B2

(12) United States Patent
Yekkirala et al.

(10) Patent No.: US 11,464,772 B2
(45) Date of Patent: Oct. 11, 2022

(54) METHODS OF TREATING ACUTE OR CHRONIC PAIN

(71) Applicant: Blue Therapeutics, Inc., Cambridge, MA (US)

(72) Inventors: Ajay Yekkirala, Canton, MA (US); David Roberson, Cambridge, MA (US); Michio Painter, Cambridge, MA (US)

(73) Assignee: Blue Therapeutics, Inc., Cambridge, MA (US)

( * ) Notice: Subject to any disclaimer, the term of this patent is extended or adjusted under 35 U.S.C. 154(b) by 0 days.

(21) Appl. No.: 16/753,509

(22) PCT Filed: Oct. 8, 2018

(86) PCT No.: PCT/US2018/054884
§ 371 (c)(1),
(2) Date: Apr. 3, 2020

(87) PCT Pub. No.: WO2019/071264
PCT Pub. Date: Apr. 11, 2019

(65) Prior Publication Data
US 2020/0289500 A1     Sep. 17, 2020

Related U.S. Application Data

(60) Provisional application No. 62/569,315, filed on Oct. 6, 2017.

(51) Int. Cl.
*A61K 31/485*     (2006.01)
*A61P 29/00*      (2006.01)

(52) U.S. Cl.
CPC ............ *A61K 31/485* (2013.01); *A61P 29/00* (2018.01)

(58) Field of Classification Search
CPC ......... A61K 31/485; A61P 25/02; A61P 25/04
USPC ....................................................... 514/282
See application file for complete search history.

(56) References Cited

U.S. PATENT DOCUMENTS

| | | |
|---|---|---|
| 4,559,157 A | 12/1985 | Smith et al. |
| 4,608,392 A | 8/1986 | Jacquet et al. |
| 4,820,508 A | 4/1989 | Wortzman |
| 4,938,949 A | 7/1990 | Borch et al. |
| 4,992,478 A | 2/1991 | Geria |
| 8,609,682 B2 | 12/2013 | Portoghese et al. |
| 8,772,308 B2 * | 7/2014 | Zhang .................... A61P 25/32 514/282 |
| 2011/0251227 A1 | 10/2011 | Portoghese |
| 2015/0141451 A1 | 5/2015 | Kandula |

FOREIGN PATENT DOCUMENTS

WO    WO 2016/138142 A1    9/2016

OTHER PUBLICATIONS

Arnér and Meyerson, "Lack of analgesic effect of opioids on neuropathic and idiopathic forms of pain," Pain, 1988, 33:11-23.
Ballantyne, J.C., "Opioid Analgesia: Perspectives on Right Use and Utility," Pain Physician, 2007, 10:479-491.
Ballantyne and Mao, "Opioid Therapy for Chronic Pain," N Engl J Med. 2003, 349(20):1943-1953.
Brennan et al., "Characterization of a rat model of incisional pain," Pain, 1996, 64:493-501.
Chaplan et al., "Quantitative assessment of tactile allodynia in the rat paw," J Neurosci Methods, 1994, 53:55-63.
Chou et al., "Research Gaps on Use of Opioids for Chronic Noncancer Pain: Findings From a Review of the Evidence for an American Pain Society and American Academy of Pain Medicine Clinical Practice Guideline," The Journal of Pain, 2009, 10(2):147-159.
Costigan et al., "Neuropathic Pain: A Maladaptive Response of the Nervous System to Damage," Annual Review of Neuroscience, 2009, 32:1-32.
Decosterd and Woolf, "Spared nerve injury: an animal model of persistent peripheral neuropathic pain," Pain, 2000, 87:149-158.
Dellemijn, P., "Are opioids effective in relieving neuropathic pain?" Pain, 1999, 80: 453-462.
Dubner, R., "A call for more science, not more rhetoric, regarding opioids and neuropathic pain," Pain 1991, 47:1-2.
Field et al., "Detection of static and dynamic components of mechanical allodynia in rat models of neuropathic pain: are they signalled by distinct primary sensory neurones?" Pain, 1999, 83: 303-311.
Fields, H.L., "Can opiates relieve neuropathic pain?," Pain, 1988, 35:365.
Geber et al., "Revised Definition of Neuropathic Pain and Its Grading System: An Open Case Series Illustrating Its Use in Clinical Practice," Am J Med., 2009, 122(10 Suppl):S3-12.
Hargreaves et al., "A new and sensitive method for measuring thermal nociception in cutaneous hyperalgesia," Pain, 1988, 32:77-88.
Jones and Loftus, "Avoiding the Vicious Cycle of Prolonged Opioid Use in Crohn's Disease," Am J Gastroenterol., 2005, 100:2230-2232.
Kidd and Urban, "Mechanisms of inflammatory pain," Br. J. Anesthesiology, 2001; 87(1): 3-11.
Kim and Chung, "An experimental model for peripheral neuropathy produced by segmental spinal nerve ligation in the rat," Pain, 1992, 50: 355-363.
Lowry et al., "Protein Measurement with the Folin Phenol Reagent," J. Biol. Chem., 1951, 193:265-275.
McQuay, H.J., "Opioid use in chronic pain," Acta Anaesthesiol Scand 1997, 41:175-183.
Portenoy et al., "The nature of opioid responsiveness and its implications for neuropathic pain: new hypotheses derived from studies of opioid infusions," Pain, 1990, 43:273-286.

(Continued)

*Primary Examiner* — Charanjit Aulakh
(74) *Attorney, Agent, or Firm* — Cooley LLP; Heidi A. Erlacher; Christine E. Dunne (57) ABSTRACT

The invention provides methods for treating chronic and acute pain. For example, the invention provides methods of treating neuropathic and inflammatory pain.

13 Claims, 3 Drawing Sheets

(56) References Cited

OTHER PUBLICATIONS

Sullivan et al., "Trends in use of opioids for non-cancer pain conditions 2000-2005 in commercial and Medicaid insurance plans: the TROUP study," Pain, 2008, 138:440-449.
Treede et al., "Neuropathic pain: redefinition and a grading system for clinical and research purposes," J. Neurology. 2008, 70(18):1630-1635.
Vissers et al., "Pharmacological correlation between the formalin test and the neuropathic pain behavior in different species with chronic constriction injury," Pharmacol Biochem Behav., 2006, 84:479-486.
Waldhoer et al., "A heterodimer-selective agonist shows in vivo relevance of G protein-coupled receptor dimers," PNAS, Jun. 2005, 102(25): 9050-9055.
Wall, P.D., "Neuropathic pain," Pain, 1990, 43:267-268.
Werling et al., "Opioid binding to rat and guinea-pig neural membranes in the presence of physiological cations at 37 degrees C," J. Pharmacol. Exp. Ther., 1985, 233, 722-728.
Werner et al., "Effects of Gabapentin in Acute Inflammatory Pain in Humans," Reg Anesth Pain Med. 2001;26(4):322-328.
Woolf, C.J., "Evidence for a central component of post-injury pain hypersensitivity," Nature, 1983, 306:686-688.
Yekkirala, A.S., "Two to tango: GPCR oligomers and GPCR-TRP channel interactions in nociception," Life Sciences, 2013, 92: 438-445.
Yekkirala et al., "Breaking barriers to novel analgesic drug development," Nat. Rev. Drug Discov. (2017) 16, 545-564.
Yekkirala et al., "N-naphthoyl-β-naltrexamine (NNTA), a highly selective and potent activator of μ/κ-opioid heteromers," PNAS, Mar. 2011, 108(12):5098-5103.
Yekkirala et al., "Standard Opioid Agonists Activate Heteromeric Opioid Receptors: Evidence for Morphine and [d-Ala2-MePhe4-Glyol5]Enkephalin as Selective μ-δ Agonists," ACS Chemical Neuroscience 2010, 1(2):146-154.
Jensen et al., "A new definition of neuropathic pain," Pain, 2011, 152: 2204-2205.
Kosek et al., "Do we need a third mechanistic descriptor for chronic pain states?" Pain (2016) 157: 1382-1386.
Nicholson, B., "Differential Diagnosis: Nociceptive and Neuropathic Pain," Am J Manag Care. 2006; 12:S256-S262.
Adams, JE, "Naloxone reversal of analgesia produced by brain stimulation in the human", Pain, vol. 2, Issue 2, Jun. 1976, pp. 161-166.
Lewanowitsch et al., "Naloxone methiodide reverses opiod-induced respiratory depression and analgesia without withdrawal", European Journal of Pharmacalogy, vol. 445, Issues 1-2, Jun. 2002, pp. 61-67.
Liu et al., "Low-Dose Naloxone Reverses Opiod-Induced Constipation and Analgesia", Journal of Pain and Symptom Management, vol. 23, Issue 1, Jan. 2002, pp. 48-53.
Manning et al., "Morphine analgesia in the formain test: reversal by mocroinjection of quaternary naloxone into the posterior hypothalamic area or periaqueductal gray", Behavioural Brain Research 92, Apr. 1998, pp. 97-102.
National Institute of Drug Abuse, "Naloxone DrugFacts", DrugFacts revised Jan. 2022, <https://www.drugabuse.gov/publications/drugfacts/naloxone>, 7 pages.
National Institute of Drug Abuse, "Naloxone for Opiod Overdose: Life-Saving Science", Mar. 2017, <https://www.drugabuse.gov/publications/naloxone-opioid-overdose-life-saving-science>, 2 pages.
Taylor et al., "Naloxone-Reversible Modulation of Pain Circuitry by Left Prefrontal rTMS", Neuropsychopharmacology 38, Jan. 2013, pp. 1189-1197.

* cited by examiner

FIGURE 1

METHODS OF TREATING ACUTE OR CHRONIC PAIN

RELATED APPLICATIONS

The application is a U.S. National Phase application, filed under 35 U.S.C. § 371, of International Application No. PCT/US2018/054884, filed Oct. 8, 2018, which claims priority to, and the benefit of, U.S. Provisional Application No. 62/569,315, filed on Oct. 6, 2017, the entire contents of each of which are incorporated herein by reference in their entireties.

BACKGROUND

There are many different types of pain conditions and syndromes. Broadly speaking, pain can be classified as nociceptive, adaptive (or protective), or maladaptive (or pathological). Within these classifications pain can be sub-categorized into acute and chronic pain states, depending on the general duration of symptoms, and then further subdivided into specific categories. Some examples include, but are not limited to, neuropathic pain, somatic pain, visceral pain, cutaneous pain, ocular pain, post-injury pain, post-operative pain, diabetic neuropathy-induced pain, inflammatory pain, arthritic pain, and cancer pain. Each of these conditions is considered separate in the eyes of a skilled person, manifesting clinically with distinct symptoms over different periods of time, and each arising through distinct biological mechanisms. The existence of distinct biological mechanisms of pain is evidenced by the use of a large number of different animal models for testing potential therapeutics. This demonstrates the skilled person's desire to match the mechanism of action of a potential therapeutic to a particular disease state, as well as to mirror the specific biological mechanisms present in the human condition.

Furthermore, depending on the type of pain, different medications are prescribed with varying and often unpredictable degrees of success. Accordingly, there is a need for improved methods of treating specific types of chronic and acute pain.

SUMMARY

Provided herein are methods of treating chronic pain in an animal, comprising administering to the animal an amount of Compound A, (A)

or a pharmaceutically acceptable salt thereof.

Also provided herein are methods of treating acute pain in an animal comprising administering to the animal an amount of Compound A, (A)

or a pharmaceutically acceptable salt thereof.

Also provided herein is Compound A, (A)

for use in treating chronic pain in an animal.

Also provided herein is Compound A, (A)

for use in the manufacture of a medicament for treating chronic pain in an animal.

Also provided herein is Compound A, (A)

for use in treating acute pain in an animal.

Also provided herein is Compound A, (A)

for use in the manufacture of a medicament for treating acute pain in an animal.

DETAILED DESCRIPTION

Physically associated receptor complexes, collectively called homomers (complexes of similar receptors) or heteromers (complexes of different receptors) depending on their composition, represent a new class of targets that can have novel and unique physiological effects when compared with the individual receptors forming the complexes (Yekkirala A S, Kalyuzhny A E, Portoghese P S. ACS Chemical Neuroscience 2010, 1(2):146-154, doi:10.1021/cn9000236; Yekkirala A S. Life Sci. 2013, 92: 438-445; Yekkirala A S, Roberson D P, Bean B P, and Woolf C J (2017) Nat. Rev. Drug Discov. 16, 545-564). N-naphthoyl-β-naltrexamine (NNTA, Compound A) is a first-in-class activator or agonist for a novel target, mu-kappa opioid receptor heteromers with picomolar binding affinity and functional potency at those receptors (Yekkirala A S, Lunzer M M, McCurdy C R, et al. Proc. Natl. Acad. Sci. USA 2011, 108(12):5098-5103, doi: 10.1073/pnas.1016277108; Portoghese, P S and Yekkirala, A S. U.S. Pat. No. 8,609,682, "US '682"). US '682 discloses that compound A is useful as an analgesic against nociceptive pain with reduced dependence, tolerance, and constipation relative to morphine. As discussed in more detail below, nociceptive pain is distinct from other types of pain, such as inflammatory pain, chemotherapy-induced pain, pain experienced post-surgery, and neuropathic pain. At present, there is no evidence to suggest that ligands targeting mu-kappa opioid receptor heteromers can produce any effect on chronic pain such as, for example, neuropathic pain, pain experienced post-surgery, inflammatory pain, or chemotherapy-induced pain. In addition, opioids such as morphine, as a class of compounds, are not effective for treating specialized pain syndromes such as, for example, neuropathic pain, or chemotherapy-induced pain. The foregoing suggests that neither the mechanistic target nor the overall compound class has been shown to be effective in chronic pain situations, making the use of Compound A in such conditions inventive. The present application discloses, for the first time, that Compound A is effective for treating various types of chronic and acute pain, including neuropathic pain, pain experienced post-surgery, inflammatory pain, or chemotherapy-induced pain, that are not amenable to treatment with other known analgesics.

Nociceptive Pain

Nociceptive pain is activated in response to underlying tissue damage, injury, or a stimulus that has the potential to cause injury. Here, a stimulus acts directly on peripheral nociceptors to begin the transmission of pain. After activation of nociceptors by noxious stimuli, this information can be relayed through the nervous system by A-delta fibers, which are thinly myelinated and relatively fast, or also by unmyelinated C-fibers, which are not myelinated and relatively slow. This sensory information is transmitted through primary afferent neurons, and then through second-order neurons such as in the spinal cord, before the message is conveyed to the brain, where the pain is ultimately perceived. Clinically, acute nociceptive pain has an underlying cause, lasts for less than 6 months, and resolves after the underlying injury or stimulus has been removed or repaired. Examples where nociceptive pain may be present include, but are not limited to, common sports injuries such as sprains and strains, post-operative pain (pain that results from surgical procedures), pain resulting from tissue trauma, burn pain, and ischemic pain or vascular pain. Nociceptive pain is represented in scientific research by various animal models, including the tail-flick model used in rats. Nociceptive pain is distinct from but often accompanied by inflammatory pain, which can arise upon activation of the immune system in response to tissue damage, injury, or a noxious stimulus.

Inflammatory Pain

One major grouping of pain diseases falls under the umbrella of inflammatory pain, or pain arising from inflammation in the body. Indeed, one of the cardinal features of inflammation in the body is the pain evoked by stimuli that are not normally noxious (called allodynia). In addition, noxious stimuli also can show enhanced pain response (called hypersensitivity). Classic examples of inflammatory pain in humans are rheumatoid arthritis, osteoarthritis, post-injury inflammatory pain and pancreatic inflammatory pain or pancreatitis pain.

From a mechanistic standpoint, inflammation of tissue injury is associated with the release of several immune mediators—bradykinin, histamine, 5-hydroxytryptamine (5-HT), ATP and nitric oxide, to name a few. The pathways they activate lead to the recruitment of immune cells that release additional cytokines, chemokines and other endogenous ligands that are algogenic (pain-inducing), resulting in the sensation of pain (Kidd B L and Urban L A. Br. J. Anesthesiology 2001; 87: 3-11). The continued presence and secretion of these ligands causes a hypersensitivity of the sensory neurons near the site of initial insult, which is also called peripheral sensitization. A prolonged state of peripheral sensitization can lead to sensitization of the entire central nociceptive pathway or 'central' sensitization (Woolf C J. Nature 1983; 306: 686-8). It is a combination of these mechanisms that leads to chronic pain in an animal.

Given such mechanistic insight, it is important to consider that inflammatory pain syndromes are refractory to several commonly used analgesics such as opioids (Sullivan M D, Edlund M J, Fan M-Y, et al. Pain 2008, 138:440-449; Jones J L, Loftus E V. Am J Gastroenterol. 2005, 100:2230-2232; Ballantyne J C, Mao J. N Engl J Med. 2003, 349:1943-1953; Chou R, Ballantyne J C, Fanciullo G J, et al. J Pain 2009, 10:147-159; Ballantyne J C. Pain Physician 2007, 10:479-491). In addition, NSAIDs, while effective for immediate pain relief, possess severe GI and cardiac side effects that limit their prolonged use (Kidd B L and Urban L A. Br. J. Anesthesiology 2001; 87: 3-11). It should also be noted that the effect of Gabapentin (or Neurontin), which is used to treat neuropathic pain, is also ambiguous for inflammatory pain (Werner M U, Perkins F M, Holte K, Pedersen J L, Kehlet H. Reg Anesth Pain Med. 2001; 26(4):322-8). All of these point clearly to the distinctiveness of this particular set of chronic pain syndromes.

Neuropathic Pain

In contrast to nociceptive pain and inflammatory pain, neuropathic pain is a pathological state of pain that is triggered by the alteration of the somatosensory nervous system. Neuropathic pain is not a protective response, but rather a disease state in which pain can occur spontaneously and in response to normally innocuous stimuli. In patients, neuropathic pain can manifest as shooting or burning sensations, is often categorized by the location of the pain, and can wax and wane throughout a day or a lifetime. Biologically, neuropathic pain is indicative of a malfunctioning nervous system. These changes can include alterations in action potentials, synaptic transmission and neural circuitry [Costigan M, Scholz J, Woolf C J. Annual review of neuroscience 2009, 32:1-32, doi:10.1146/annurev.neuro.051508.135531]. Neuropathic pain can be triggered by alcoholism, amputation, chemotherapy, diabetes, HIV infection, multiple myeloma, multiple sclerosis, damage to the nervous system, shingles, syphilis, thyroid issues, post-herpetic neuralgia, back pain, cancer neuropathy, phantom limb pain, and carpal tunnel syndrome. Neuropathic pain can involve persistent, spontaneous pain as well as allodynia. Neuropathic pain also can be characterized by hyperalgesia, in which there is an accentuated response to a painful stimulus that usually is trivial, such as a pin prick. Neuropathic pain is notoriously difficult to treat and often refractory to all available medications (Dubner R. Pain 1991, 47:1-2; Fields H L. Pain 1988, 35:365-7; Arner S, Meyerson B A. Pain 1988, 33:11-23; Dellemijn P. Pain 1999, 80: 453-62; McQuay H J. Acta Anaesthesiol Scand 1997, 41:175-83; Wall P D. Pain 1990, 43:267-8; Portenoy R K, Foley K M, Inturrisi C E. Pain 1990, 43:273-86). In addition, current therapies have serious side-effects including, for example, cognitive changes, sedation, nausea and, in the case of narcotic drugs, addiction. Many patients suffering from neuropathic pain are elderly or have other medical conditions that particularly limit their tolerance of the side-effects associated with available drug therapy. The inadequacy of current therapy in relieving neuropathic pain without producing intolerable side-effects frequently is manifest in the depression and suicidal tendency of chronic pain sufferers. Common animal models of neuropathic pain include, but are not limited to, the formalin test, spared nerve injury, chronic constriction injury and sciatic nerve ligation.

A cardinal symptom of neuropathic pain is allodynia (Geber C, Baumgärtner U, Schwab R, Müller H, Stoeter P, Dieterich M, Sommer C, Birklein F, Treede R D. Am J Med. 2009 October, 122 (10 Suppl): 53-12. doi: 10.1016/j.amjmed.2009.04.005; Treede R D, Jensen T S, Campbell J N, Cruccu G, Dostrovsky J O, Griffin J W, Hansson P, Hughes R, Nurmikko T, Serra J. Neurology. 2008 Apr. 29, 70(18):1630-5), which is pain or a pain-like response caused by a mechanical, thermal (warm or cool) or other sensory stimulus that is not normally painful. Mechanical stimuli that produce allodynia can be broadly classified as dynamic or static. Static mechanical allodynia occurs when pain is evoked by a stationary (non-moving) mechanical stimulus that does not normally produce pain, while dynamic allodynia is described as pain in response to being stroked lightly in a manner that is not normally painful. Animal models have been developed that produce symptoms of allodynia, including static mechanical allodynia, dynamic mechanical allodynia, or thermal allodynia via laboratory-induced disease models, chemical injury or nerve trauma in animals, such as rodents. Importantly, morphine is capable of blocking only static allodynia, and not dynamic allodynia, in rat models of neuropathic pain. In contrast, pregablin, which is now considered the standard of care for many types of neuropathic pain, is capable of blocking both types of allodynia (Field M J, Bramwell S, Hughes J, Singh L. *Pain*. 1999, 83(2): 303-311). Such studies demonstrate the difference in mechanism between neuropathic pain and other types of pain that are better treated by standard mu-opioids.

Methods, Compounds and Uses for Treating Pain

Provided herein are methods of treating chronic pain in an animal, comprising administering to the animal an amount of Compound A, (A)

or a pharmaceutically acceptable salt thereof. In some embodiments, the chronic pain is neuropathic pain. In some embodiments, the neuropathic pain is diabetic neuropathy-induced pain. In some embodiments, the neuropathic pain is chemotherapy-induced pain. In some embodiments, the neuropathic pain is sciatica pain. In some embodiments, the neuropathic pain is carpal tunnel syndrome pain. In some embodiments, the neuropathic pain is trigeminal neuralgia pain. In some embodiments, the neuropathic pain is fibromyalgia pain. In some embodiments, the neuropathic pain is post-herpetic neuralgia pain.

In some embodiments, the chronic pain is inflammatory pain. In some embodiments, the inflammatory pain is somatic pain. In some embodiments, the inflammatory pain is rheumatoid arthritis pain. In some embodiments, the inflammatory pain is pain associated with rheumatoid arthritis. In some embodiments, the inflammatory pain is osteoarthritis pain. In some embodiments, the inflammatory pain is autoimmune disorder related pain. In some embodiments, the inflammatory pain is pain associated with an autoimmune disorder. In some embodiments, the inflammatory pain is cancer pain. In some embodiments, the inflammatory pain is pain associated with cancer. In some embodiments, the inflammatory pain is post-surgical pain. In some embodiments, the inflammatory pain is post-injury pain. In some embodiments, the animal treated for chronic pain is a human.

Also provided herein are methods of treating acute pain in an animal comprising administering to the animal an amount of Compound A, (A)

or a pharmaceutically acceptable salt thereof. In some embodiments, the acute pain is neuropathic pain. In some embodiments, the neuropathic pain is diabetic neuropathy-induced pain. In some embodiments, the neuropathic pain is chemotherapy-induced pain. In some embodiments, the neuropathic pain is sciatica pain. In some embodiments, the neuropathic pain is carpal tunnel syndrome pain. In some embodiments, the neuropathic pain is trigeminal neuralgia pain. In some embodiments, the neuropathic pain is fibromyalgia pain. In some embodiments, the neuropathic pain is post-herpetic neuralgia pain.

In some embodiments, the acute pain is inflammatory pain. In some embodiments, the inflammatory pain is somatic pain. In some embodiments, the inflammatory pain is rheumatoid arthritis pain. In some embodiments, the inflammatory pain is pain associated with rheumatoid arthritis. In some embodiments, the inflammatory pain is osteoarthritis pain. In some embodiments, the inflammatory pain is autoimmune disorder related pain. In some embodiments, the inflammatory pain is pain associated with an autoimmune disorder. In some embodiments, the inflammatory pain is cancer pain. In some embodiments, the inflammatory pain is pain associated with cancer. In some embodiments, the inflammatory pain is post-surgical pain. In some embodiments, the inflammatory pain is post-injury pain. In some embodiments, the animal treated for acute pain is a human.

The application also provides Compound A or a pharmaceutically acceptable salt thereof for use in treating chronic pain in an animal. In some embodiments, the chronic pain is neuropathic pain. In some embodiments, the neuropathic pain is diabetic neuropathy-induced pain. In some embodiments, the neuropathic pain is chemotherapy-induced pain. In some embodiments, the neuropathic pain is sciatica pain. In some embodiments, the neuropathic pain is carpal tunnel syndrome pain. In some embodiments, the neuropathic pain is trigeminal neuralgia pain. In some embodiments, the neuropathic pain is fibromyalgia pain. In some embodiments, the neuropathic pain is post-herpetic neuralgia pain. In some embodiments, the chronic pain is inflammatory pain. In some embodiments, the inflammatory pain is somatic pain. In some embodiments, the inflammatory pain is rheumatoid arthritis pain. In some embodiments, the inflammatory pain is pain associated with rheumatoid arthritis. In some embodiments, the inflammatory pain is osteoarthritis pain. In some embodiments, the inflammatory pain is autoimmune disorder related pain. In some embodiments, the inflammatory pain is pain associated with an autoimmune disorder. In some embodiments, the inflammatory pain is cancer pain. In some embodiments, the inflammatory pain is pain associated with cancer. In some embodiments, the inflammatory pain is post-surgical pain. In some embodiments, the inflammatory pain is post-injury pain. In some embodiments, the animal treated for chronic pain is a human.

The application also provides Compound A or a pharmaceutically acceptable salt thereof for use in treating acute pain in an animal. In some embodiments, the acute pain is neuropathic pain. In some embodiments, the neuropathic pain is diabetic neuropathy-induced pain. In some embodiments, the neuropathic pain is chemotherapy-induced pain. In some embodiments, the neuropathic pain is sciatica pain. In some embodiments, the neuropathic pain is carpal tunnel syndrome pain. In some embodiments, the neuropathic pain is trigeminal neuralgia pain. In some embodiments, the neuropathic pain is fibromyalgia pain. In some embodiments, the neuropathic pain is post-herpetic neuralgia pain. In some embodiments, the acute pain is inflammatory pain. In some embodiments, the inflammatory pain is somatic pain. In some embodiments, the inflammatory pain is rheumatoid arthritis pain. In some embodiments, the inflammatory pain is pain associated with rheumatoid arthritis. In some embodiments, the inflammatory pain is osteoarthritis pain. In some embodiments, the inflammatory pain is autoimmune disorder related pain. In some embodiments, the inflammatory pain is pain associated with an autoimmune disorder. In some embodiments, the inflammatory pain is cancer pain. In some embodiments, the inflammatory pain is pain associated with cancer. In some embodiments, the inflammatory pain is post-surgical pain. In some embodiments, the inflammatory pain is post-injury pain. In some embodiments, the animal treated for acute pain is a human.

The application also provides Compound A or a pharmaceutically acceptable salt thereof for use in the manufacture of a medicament for treating chronic pain in an animal. In some embodiments, the chronic pain is neuropathic pain. In some embodiments, the neuropathic pain is diabetic neuropathy-induced pain. In some embodiments, the neuropathic pain is chemotherapy-induced pain. In some embodiments, the neuropathic pain is sciatica pain. In some embodiments, the neuropathic pain is carpal tunnel syndrome pain. In some embodiments, the neuropathic pain is trigeminal neuralgia pain. In some embodiments, the neuropathic pain is fibromyalgia pain. In some embodiments, the neuropathic pain is post-herpetic neuralgia pain. In some embodiments, the chronic pain is inflammatory pain. In some embodiments, the inflammatory pain is somatic pain. In some embodiments, the inflammatory pain is rheumatoid arthritis pain. In some embodiments, the inflammatory pain is pain associated with rheumatoid arthritis. In some embodiments, the inflammatory pain is osteoarthritis pain. In some embodiments, the inflammatory pain is autoimmune disorder related pain. In some embodiments, the inflammatory pain is pain associated with an autoimmune disorder. In some embodiments, the inflammatory pain is cancer pain. In some embodiments, the inflammatory pain is pain associated with cancer. In some embodiments, the inflammatory pain is post-surgical pain. In some embodiments, the inflammatory pain is post-injury pain. In some embodiments, the animal treated for chronic pain is a human.

The application also provides Compound A or a pharmaceutically acceptable salt thereof for use in the manufacture of a medicament for treating acute pain in an animal. In some embodiments, the acute pain is neuropathic pain. In some embodiments, the neuropathic pain is diabetic neuropathy-induced pain. In some embodiments, the neuropathic pain is chemotherapy-induced pain. In some embodiments, the neuropathic pain is sciatica pain. In some embodiments, the neuropathic pain is carpal tunnel syndrome pain. In some embodiments, the neuropathic pain is trigeminal neuralgia pain. In some embodiments, the neuropathic pain is fibromyalgia pain. In some embodiments, the neuropathic pain is post-herpetic neuralgia pain. In some embodiments, the acute pain is inflammatory pain. In some embodiments, the inflammatory pain is somatic pain. In some embodiments, the inflammatory pain is rheumatoid arthritis pain. In some embodiments, the inflammatory pain is pain associated with rheumatoid arthritis. In some embodiments, the inflammatory pain is osteoarthritis pain. In some embodiments, the inflammatory pain is autoimmune disorder related pain. In some embodiments, the inflammatory pain is pain associated with an autoimmune disorder. In some embodiments, the inflammatory pain is cancer pain. In some embodiments, the inflammatory pain is pain associated with cancer. In some embodiments, the inflammatory pain is post-surgical pain. In some embodiments, the inflammatory pain is post-injury pain. In some embodiments, the animal treated for acute pain is a human.

In some embodiments of the methods and compounds of the disclosure, about 100 mcg of Compound A or a pharmaceutically acceptable salt thereof is administered or is suitable for administration once a day. In some embodiments, about 100 mcg of Compound A or a pharmaceutically acceptable salt thereof is administered or is suitable for administration twice a day. In some embodiments, about 100 mcg of Compound A or a pharmaceutically acceptable salt thereof is administered or is suitable for administration three times a day. In some embodiments, about 100 mcg of Compound A or a pharmaceutically acceptable salt thereof is administered or is suitable for administration four times a day. In some embodiments, about 100 mcg of Compound A or a pharmaceutically acceptable salt thereof is administered or is suitable for administration five times a day.

In some embodiments of the methods and compounds of the disclosure, about 1 mg of Compound A or a pharmaceutically acceptable salt thereof is administered or is suitable for administration once a day. In some embodiments, about 1 mg of Compound A or a pharmaceutically acceptable salt thereof is administered or is suitable for administration twice a day. In some embodiments, about 1 mg of Compound A or a pharmaceutically acceptable salt thereof is administered or is suitable for administration three times a day. In some embodiments, about 1 mg of Compound A or a pharmaceutically acceptable salt thereof is administered or is suitable for administration four times a day. In some embodiments, about 1 mg of Compound A or a pharmaceutically acceptable salt thereof is administered or is suitable for administration five times a day.

In some embodiments of the methods and compounds of the disclosure, about 2 mg of Compound A or a pharmaceutically acceptable salt thereof is administered or is suitable for administration once a day. In some embodiments, about 2 mg of Compound A or a pharmaceutically acceptable salt thereof is administered or is suitable for administration twice a day. In some embodiments, about 2 mg of Compound A or a pharmaceutically acceptable salt thereof is administered or is suitable for administration three times a day. In some embodiments, about 2 mg of Compound A or a pharmaceutically acceptable salt thereof is administered or is suitable for administration four times a day. In some embodiments, about 2 mg of Compound A or a pharmaceutically acceptable salt thereof is administered or is suitable for administration five times a day.

In some embodiments of the methods and compounds of the disclosure, about 3 mg of Compound A or a pharmaceutically acceptable salt thereof is administered or is suitable for administration once a day. In some embodiments, about 3 mg of Compound A or a pharmaceutically acceptable salt thereof is administered or is suitable for administration twice a day. In some embodiments, about 3 mg of Compound A or a pharmaceutically acceptable salt thereof is administered or is suitable for administration three times a day. In some embodiments, about 3 mg of Compound A or a pharmaceutically acceptable salt thereof is administered or is suitable for administration four times a day. In some embodiments, about 3 mg of Compound A or a pharmaceutically acceptable salt thereof is administered or is suitable for administration five times a day.

In some embodiments of the methods and compounds of the disclosure, about 4 mg of Compound A or a pharmaceutically acceptable salt thereof is administered or is suitable for administration once a day. In some embodiments, about 4 mg of Compound A or a pharmaceutically acceptable salt thereof is administered or is suitable for administration twice a day. In some embodiments, about 4 mg of Compound A or a pharmaceutically acceptable salt thereof is administered or is suitable for administration three times a day. In some embodiments, about 4 mg of Compound A or a pharmaceutically acceptable salt thereof is administered or is suitable for administration four times a day. In some embodiments, about 4 mg of Compound A or a pharmaceutically acceptable salt thereof is administered or is suitable for administration five times a day.

In some embodiments of the methods and compounds of the disclosure, about 5 mg of Compound A or a pharmaceutically acceptable salt thereof is administered or is suitable for administration once a day. In some embodiments, about 5 mg of Compound A or a pharmaceutically acceptable salt thereof is administered or is suitable for administration twice a day. In some embodiments, about 5 mg of Compound A or a pharmaceutically acceptable salt thereof is administered or is suitable for administration three times a day. In some embodiments, about 5 mg of Compound A or a pharmaceutically acceptable salt thereof is administered or is suitable for administration four times a day. In some embodiments, about 5 mg of Compound A or a pharmaceutically acceptable salt thereof is administered or is suitable for administration five times a day.

In some embodiments of the methods and compounds of the disclosure, about 6 mg of Compound A or a pharmaceutically acceptable salt thereof is administered or is suitable for administration once a day. In some embodiments, about 6 mg of Compound A or a pharmaceutically acceptable salt thereof is administered or is suitable for administration twice a day. In some embodiments, about 6 mg of Compound A or a pharmaceutically acceptable salt thereof is administered or is suitable for administration three times a day. In some embodiments, about 6 mg of Compound A or a pharmaceutically acceptable salt thereof is administered or is suitable for administration four times a day. In some embodiments, about 6 mg of Compound A or a pharmaceutically acceptable salt thereof is administered or is suitable for administration five times a day.

In some embodiments of the methods and compounds of the disclosure, about 7 mg of Compound A or a pharmaceutically acceptable salt thereof is administered or is suitable for administration once a day. In some embodiments, about 7 mg of Compound A or a pharmaceutically acceptable salt thereof is administered or is suitable for administration twice a day. In some embodiments, about 7 mg of Compound A or a pharmaceutically acceptable salt thereof is administered or is suitable for administration three times a day. In some embodiments, about 7 mg of Compound A or a pharmaceutically acceptable salt thereof is administered or is suitable for administration four times a day. In some embodiments, about 7 mg of Compound A or a pharmaceutically acceptable salt thereof is administered or is suitable for administration five times a day.

In some embodiments of the methods and compounds of the disclosure, about 8 mg of Compound A or a pharmaceutically acceptable salt thereof is administered or is suitable for administration once a day. In some embodiments, about 8 mg of Compound A or a pharmaceutically acceptable salt thereof is administered or is suitable for administration twice a day. In some embodiments, about 8 mg of Compound A or a pharmaceutically acceptable salt thereof is administered or is suitable for administration three times a day. In some embodiments, about 8 mg of Compound A or a pharmaceutically acceptable salt thereof is administered or is suitable for administration four times a day. In some embodiments, about 8 mg of Compound A or a pharmaceutically acceptable salt thereof is administered or is suitable for administration five times a day.

In some embodiments of the methods and compounds of the disclosure, about 9 mg of Compound A or a pharmaceutically acceptable salt thereof is administered or is suitable for administration once a day. In some embodiments, about 9 mg of Compound A or a pharmaceutically acceptable salt thereof is administered or is suitable for administration twice a day. In some embodiments, about 9 mg of Compound A or a pharmaceutically acceptable salt thereof is administered or is suitable for administration three times a day. In some embodiments, about 9 mg of Compound A or a pharmaceutically acceptable salt thereof is administered or is suitable for administration four times a day. In some embodiments, about 9 mg of Compound A or a pharmaceutically acceptable salt thereof is administered or is suitable for administration five times a day.

In some embodiments of the methods and compounds of the disclosure, about 10 mg of Compound A or a pharmaceutically acceptable salt thereof is administered or is suitable for administration once a day. In some embodiments, about 10 mg of Compound A or a pharmaceutically acceptable salt thereof is administered or is suitable for administration twice a day. In some embodiments, about 10 mg of Compound A or a pharmaceutically acceptable salt thereof is administered or is suitable for administration three times a day. In some embodiments, about 10 mg of Compound A or a pharmaceutically acceptable salt thereof is administered or is suitable for administration four times a day. In some embodiments, about 10 mg of Compound A or a pharmaceutically acceptable salt thereof is administered or is suitable for administration five times a day.

In some embodiments of the methods and compounds of the disclosure, about 15 mg of Compound A or a pharmaceutically acceptable salt thereof is administered or is suitable for administration once a day. In some embodiments, about 15 mg of Compound A or a pharmaceutically acceptable salt thereof is administered or is suitable for administration twice a day. In some embodiments, about 15 mg of Compound A or a pharmaceutically acceptable salt thereof is administered or is suitable for administration three times a day. In some embodiments, about 15 mg of Compound A or a pharmaceutically acceptable salt thereof is administered or is suitable for administration four times a day. In some embodiments, about 15 mg of Compound A or a pharmaceutically acceptable salt thereof is administered or is suitable for administration five times a day.

In some embodiments of the methods and compounds of the disclosure, about 20 mg of Compound A or a pharmaceutically acceptable salt thereof is administered or is suitable for administration once a day. In some embodiments, about 20 mg of Compound A or a pharmaceutically acceptable salt thereof is administered or is suitable for administration twice a day. In some embodiments, about 20 mg of Compound A or a pharmaceutically acceptable salt thereof is administered or is suitable for administration three times a day. In some embodiments, about 20 mg of Compound A or a pharmaceutically acceptable salt thereof is administered or is suitable for administration four times a day. In some embodiments, about 20 mg of Compound A or a pharmaceutically acceptable salt thereof is administered or is suitable for administration five times a day.

In some embodiments of the methods and compounds of the disclosure, about 25 mg of Compound A or a pharmaceutically acceptable salt thereof is administered or is suitable for administration once a day. In some embodiments, about 25 mg of Compound A or a pharmaceutically acceptable salt thereof is administered or is suitable for administration twice a day. In some embodiments, about 25 mg of Compound A or a pharmaceutically acceptable salt thereof is administered or is suitable for administration three times a day. In some embodiments, about 25 mg of Compound A or a pharmaceutically acceptable salt thereof is administered or is suitable for administration four times a day. In some embodiments, about 25 mg of Compound A or a pharmaceutically acceptable salt thereof is administered or is suitable for administration five times a day.

In some embodiments of the methods and compounds of the disclosure, about 30 mg of Compound A or a pharmaceutically acceptable salt thereof is administered or is suitable for administration once a day. In some embodiments, about 30 mg of Compound A or a pharmaceutically acceptable salt thereof is administered or is suitable for administration twice a day. In some embodiments, about 30 mg of Compound A or a pharmaceutically acceptable salt thereof is administered or is suitable for administration three times a day. In some embodiments, about 30 mg of Compound A or a pharmaceutically acceptable salt thereof is administered or is suitable for administration four times a day. In some embodiments, about 30 mg of Compound A or a pharmaceutically acceptable salt thereof is administered or is suitable for administration five times a day.

In some embodiments of the methods and compounds of the disclosure, about 35 mg of Compound A or a pharmaceutically acceptable salt thereof is administered or is suitable for administration once a day. In some embodiments, about 35 mg of Compound A or a pharmaceutically acceptable salt thereof is administered or is suitable for administration twice a day. In some embodiments, about 35 mg of Compound A or a pharmaceutically acceptable salt thereof is administered or is suitable for administration three times a day. In some embodiments, about 35 mg of Compound A or a pharmaceutically acceptable salt thereof is administered or is suitable for administration four times a day. In some embodiments, about 35 mg of Compound A or a pharmaceutically acceptable salt thereof is administered or is suitable for administration five times a day.

In some embodiments of the methods and compounds of the disclosure, about 40 mg of Compound A or a pharmaceutically acceptable salt thereof is administered or is suitable for administration once a day. In some embodiments, about 40 mg of Compound A or a pharmaceutically acceptable salt thereof is administered or is suitable for administration twice a day. In some embodiments, about 40 mg of Compound A or a pharmaceutically acceptable salt thereof is administered or is suitable for administration three times a day. In some embodiments, about 40 mg of Compound A or a pharmaceutically acceptable salt thereof is administered or is suitable for administration four times a day. In some embodiments, about 40 mg of Compound A or a pharmaceutically acceptable salt thereof is administered or is suitable for administration five times a day.

In some embodiments of the methods and compounds of the disclosure, about 45 mg of Compound A or a pharmaceutically acceptable salt thereof is administered or is suitable for administration once a day. In some embodiments, about 45 mg of Compound A or a pharmaceutically acceptable salt thereof is administered or is suitable for administration twice a day. In some embodiments, about 45 mg of Compound A or a pharmaceutically acceptable salt thereof is administered or is suitable for administration three times a day. In some embodiments, about 45 mg of Compound A or a pharmaceutically acceptable salt thereof is administered or is suitable for administration four times a day. In some embodiments, about 45 mg of Compound A or a pharmaceutically acceptable salt thereof is administered or is suitable for administration five times a day.

In some embodiments of the methods and compounds of the disclosure, about 50 mg of Compound A or a pharmaceutically acceptable salt thereof is administered or is suitable for administration once a day. In some embodiments, about 50 mg of Compound A or a pharmaceutically acceptable salt thereof is administered or is suitable for administration twice a day. In some embodiments, about 50 mg of Compound A or a pharmaceutically acceptable salt thereof is administered or is suitable for administration three times a day. In some embodiments, about 50 mg of Compound A or a pharmaceutically acceptable salt thereof is administered or is suitable for administration four times a day. In some embodiments, about 50 mg of Compound A or a pharmaceutically acceptable salt thereof is administered or is suitable for administration five times a day.

In some embodiments of the methods and compounds of the disclosure, about 75 mg of Compound A or a pharmaceutically acceptable salt thereof is administered or is suitable for administration once a day. In some embodiments, about 75 mg of Compound A or a pharmaceutically acceptable salt thereof is administered or is suitable for administration twice a day. In some embodiments, about 75 mg of Compound A or a pharmaceutically acceptable salt thereof is administered or is suitable for administration three times a day. In some embodiments, about 75 mg of Compound A or a pharmaceutically acceptable salt thereof is administered or is suitable for administration four times a day. In some embodiments, about 75 mg of Compound A or a pharmaceutically acceptable salt thereof is administered or is suitable for administration five times a day.

In some embodiments of the methods and compounds of the disclosure, about 100 mg of Compound A or a pharmaceutically acceptable salt thereof is administered or is suitable for administration once a day. In some embodiments, about 100 mg of Compound A or a pharmaceutically acceptable salt thereof is administered or is suitable for administration twice a day. In some embodiments, about 100 mg of Compound A or a pharmaceutically acceptable salt thereof is administered or is suitable for administration three times a day. In some embodiments, about 100 mg of Compound A or a pharmaceutically acceptable salt thereof is administered or is suitable for administration four times a day. In some embodiments, about 100 mg of Compound A or a pharmaceutically acceptable salt thereof is administered or is suitable for administration five time a day.

In some embodiments of the methods and compounds of the disclosure, about 250 mg of Compound A or a pharmaceutically acceptable salt thereof is administered or is suitable for administration once a day. In some embodiments, about 250 mg of Compound A or a pharmaceutically acceptable salt thereof is administered or is suitable for administration twice a day. In some embodiments, about 250 mg of Compound A or a pharmaceutically acceptable salt thereof is administered or is suitable for administration three times a day. In some embodiments, about 250 mg of Compound A or a pharmaceutically acceptable salt thereof is administered or is suitable for administration four times a day. In some embodiments, about 250 mg of Compound A or a pharmaceutically acceptable salt thereof is administered or is suitable for administration five times a day.

In some embodiments of the methods and compounds of the disclosure, about 25 μg/kg of Compound A or a pharmaceutically acceptable salt thereof is administered or is suitable for administration once a day. In some embodiments, about 25 μg/kg mg of Compound A or a pharmaceutically acceptable salt thereof is administered or is suitable for administration twice a day. In some embodiments, about 25 μg/kg mg of Compound A or a pharmaceutically acceptable salt thereof is administered or is suitable for administration three times a day. In some embodiments, about 25 μg/kg mg of Compound A or a pharmaceutically acceptable salt thereof is administered or is suitable for administration four times a day. In some embodiments, about 25 μg/kg mg of Compound A or a pharmaceutically acceptable salt thereof is administered or is suitable for administration five times a day.

In some embodiments of the methods and compounds of the disclosure, about 50 μg/kg of Compound A or a pharmaceutically acceptable salt thereof is administered or is suitable for administration once a day. In some embodiments, about 50 μg/kg mg of Compound A or a pharmaceutically acceptable salt thereof is administered or is suitable for administration twice a day. In some embodiments, about 50 μg/kg mg of Compound A or a pharmaceutically acceptable salt thereof is administered or is suitable for administration three times a day. In some embodiments, about 50 μg/kg mg of Compound A or a pharmaceutically acceptable salt thereof is administered or is suitable for administration four times a day. In some embodiments, about 50 μg/kg mg of Compound A or a pharmaceutically acceptable salt thereof is administered or is suitable for administration five times a day.

In some embodiments of the methods and compounds of the disclosure, about 75 μg/kg of Compound A or a pharmaceutically acceptable salt thereof is administered or is suitable for administration once a day. In some embodiments, about 75 μg/kg mg of Compound A or a pharmaceutically acceptable salt thereof is administered or is suitable for administration twice a day. In some embodiments, about 75 μg/kg mg of Compound A or a pharmaceutically acceptable salt thereof is administered or is suitable for administration three times a day. In some embodiments, about 75 μg/kg mg of Compound A or a pharmaceutically acceptable salt thereof is administered or is suitable for administration four times a day. In some embodiments, about 75 μg/kg mg of Compound A or a pharmaceutically acceptable salt thereof is administered or is suitable for administration five times a day.

In some embodiments of the methods and compounds of the disclosure, about 100 μg/kg of Compound A or a pharmaceutically acceptable salt thereof is administered or is suitable for administration once a day. In some embodiments, about 100 μg/kg mg of Compound A or a pharmaceutically acceptable salt thereof is administered or is suitable for administration twice a day. In some embodiments, about 100 μg/kg mg of Compound A or a pharmaceutically acceptable salt thereof is administered or is suitable for administration three times a day. In some embodiments, about 100 μg/kg mg of Compound A or a pharmaceutically acceptable salt thereof is administered or is suitable for administration four times a day. In some embodiments, about 100 μg/kg mg of Compound A or a pharmaceutically acceptable salt thereof is administered or is suitable for administration five times a day.

In some embodiments of the methods and compounds of the disclosure, about 200 μg/kg of Compound A or a pharmaceutically acceptable salt thereof is administered or is suitable for administration once a day. In some embodiments, about 200 μg/kg mg of Compound A or a pharmaceutically acceptable salt thereof is administered or is suitable for administration twice a day. In some embodiments, about 200 μg/kg mg of Compound A or a pharmaceutically acceptable salt thereof is administered or is suitable for administration three times a day. In some embodiments, about 200 μg/kg mg of Compound A or a pharmaceutically acceptable salt thereof is administered or is suitable for administration four times a day. In some embodiments, about 200 μg/kg mg of Compound A or a pharmaceutically acceptable salt thereof is administered or is suitable for administration five times a day.

In some embodiments of the methods and compounds of the disclosure, about 300 μg/kg of Compound A or a pharmaceutically acceptable salt thereof is administered or is suitable for administration once a day. In some embodiments, about 300 μg/kg mg of Compound A or a pharmaceutically acceptable salt thereof is administered or is suitable for administration twice a day. In some embodiments, about 300 μg/kg mg of Compound A or a pharmaceutically acceptable salt thereof is administered or is suitable for administration three times a day. In some embodiments, about 300 μg/kg mg of Compound A or a pharmaceutically acceptable salt thereof is administered or is suitable for administration four times a day. In some embodiments, about 300 μg/kg mg of Compound A or a pharmaceutically acceptable salt thereof is administered or is suitable for administration five times a day.

In some embodiments of the methods and compounds of the disclosure, about 500 μg/kg of Compound A or a pharmaceutically acceptable salt thereof is administered or is suitable for administration once a day. In some embodiments, about 500 μg/kg mg of Compound A or a pharmaceutically acceptable salt thereof is administered or is suitable for administration twice a day. In some embodiments, about 500 μg/kg mg of Compound A or a pharmaceutically acceptable salt thereof is administered or is suitable for administration three times a day. In some embodiments, about 500 μg/kg mg of Compound A or a pharmaceutically acceptable salt thereof is administered or is suitable for administration four times a day. In some embodiments, about 500 μg/kg mg of Compound A or a pharmaceutically acceptable salt thereof is administered or is suitable for administration five times a day.

In some embodiments of the methods and compounds of the disclosure, about 1 mg/kg of Compound A or a pharmaceutically acceptable salt thereof is administered or is suitable for administration once a day. In some embodiments, about 1 mg/kg of Compound A or a pharmaceutically acceptable salt thereof is administered or is suitable for administration twice a day. In some embodiments, about 1 mg/kg of Compound A or a pharmaceutically acceptable salt thereof is administered or is suitable for administration three times a day. In some embodiments, about 1 mg/kg of Compound A or a pharmaceutically acceptable salt thereof is administered or is suitable for administration four times a day. In some embodiments, about 1 mg/kg of Compound A or a pharmaceutically acceptable salt thereof is administered or is suitable for administration five times a day.

In some embodiments of the methods and compounds of the disclosure, about 5 mg/kg of Compound A or a pharmaceutically acceptable salt thereof is administered or is suitable for administration once a day. In some embodiments, about 5 mg/kg of Compound A or a pharmaceutically acceptable salt thereof is administered or is suitable for administration twice a day. In some embodiments, about 5 mg/kg of Compound A or a pharmaceutically acceptable salt thereof is administered or is suitable for administration three times a day. In some embodiments, about 5 mg/kg of Compound A or a pharmaceutically acceptable salt thereof is administered or is suitable for administration four times a day. In some embodiments, about 5 mg/kg of Compound A or a pharmaceutically acceptable salt thereof is administered or is suitable for administration five times a day.

In some embodiments of the methods and compounds of the disclosure, about 10 mg/kg of Compound A or a pharmaceutically acceptable salt thereof is administered or is suitable for administration once a day. In some embodiments, about 10 mg/kg of Compound A or a pharmaceutically acceptable salt thereof is administered or is suitable for administration twice a day. In some embodiments, about 10 mg/kg of Compound A or a pharmaceutically acceptable salt thereof is administered or is suitable for administration three times a day. In some embodiments, about 10 mg/kg of Compound A or a pharmaceutically acceptable salt thereof is administered or is suitable for administration four times a day. In some embodiments, about 10 mg/kg of Compound A or a pharmaceutically acceptable salt thereof is administered or is suitable for administration five times a day.

In some embodiments of the methods and compounds of the disclosure, about 20 mg/kg of Compound A or a pharmaceutically acceptable salt thereof is administered or is suitable for administration once a day. In some embodiments, about 20 mg/kg of Compound A or a pharmaceutically acceptable salt thereof is administered or is suitable for administration twice a day. In some embodiments, about 20 mg/kg of Compound A or a pharmaceutically acceptable salt thereof is administered or is suitable for administration three times a day. In some embodiments, about 20 mg/kg of Compound A or a pharmaceutically acceptable salt thereof is administered or is suitable for administration four times a day. In some embodiments, about 20 mg/kg of Compound A or a pharmaceutically acceptable salt thereof is administered or is suitable for administration five times a day.

In some embodiments of the methods and compounds of the disclosure, about 30 mg/kg of Compound A or a pharmaceutically acceptable salt thereof is administered or is suitable for administration once a day. In some embodiments, about 30 mg/kg of Compound A or a pharmaceutically acceptable salt thereof is administered or is suitable for administration twice a day. In some embodiments, about 30 mg/kg of Compound A or a pharmaceutically acceptable salt thereof is administered or is suitable for administration three times a day. In some embodiments, about 30 mg/kg of Compound A or a pharmaceutically acceptable salt thereof is administered or is suitable for administration four times a day. In some embodiments, about 30 mg/kg of Compound A or a pharmaceutically acceptable salt thereof is administered or is suitable for administration five times a day.

Pharmaceutical Compositions

In cases where compounds are sufficiently basic or acidic, a salt of Compound A can be useful as an intermediate for isolating or purifying Compound A. Additionally, administration of Compound A as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts. In some embodiments, Compound A is a hydrochloride salt.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compound A can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with one or more of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver Compound A to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of Compound A can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The compound is conveniently formulated in unit dosage form; for example, containing 5 to 1000 mg, conveniently 10 to 750 mg, most conveniently, 50 to 500 mg of active ingredient per unit dosage form. For example, the compound is formulated in unit dose form contain 1 mg, 10 mg, 20 mg, or 100 mg of active ingredient per unit dose form. In one embodiment, the invention provides a composition comprising Compound A formulated in such a unit dosage form.

The desired dose may be presented in a single dose per day or in multiple doses per day, for example, as two, three, four, five, or more doses per day. For example, the compound is administered in unit dose form at 100 mcg per day, 1 mg per day, 10 mg per day, 20 mg per day, or 100 mg per day. For example, the compound is administered in unit dose form at 100 mcg two, three, four, or five times daily; 1 mg two, three, four, or five times daily; 10 mg two, three, four, or five times daily; 20 mg two, three, four, or five times daily; or 100 mg two, three, four, or five times daily.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Assays for Measuring Activity

The pharmacological properties of a compound can be determined using models that are well known to the art. In cell culture, competition binding (Oliver, H. et al. (1951) J. Biol. Chem. 193, 265-275; Werling, L. L. et al. (1985) J. Pharmacol. Exp. Ther. 233, 722-728), $Ca^{2+}$ release assays (Waldhoer, M. et al. (2005) Proc. Natl. Acad. Sci. 102, 9050-9055) or [$^{35}$S]GTPγS assays (in Mullaney, I (1999) in Signal Transduction: A practical approach, 2nd ed., Oxford University Press, 100-101) can be used to assess the affinity and selectivity of a compound for the different opioid receptors.

The properties of a compound can be determined using models that are well known to the art or by the spared nerve injury (SNI), sciatic nerve ligation (SNL), rodent plantar formalin assay, rodent paw incision, Hargreaves assay, Von Frey assay, guinea pig ileum (GPI), and the rodent tail flick procedures. Compounds can be also used to pharmacologically characterize the receptors that are activated by Compound A.

The spared nerve injury model involves ligating two branches (the common perennial and tibial nerves) of either the left or right sciatic nerve, while leaving the third branch (the sural nerve) intact (Decosterd I, Woolf C J. *Pain* 2000 August, 87(2):149-58). Another rodent neuropathic pain model, called the sciatic nerve ligation model involves isolating and tying a ligature around specific lumbar spinal nerves, such as the L5 spinal nerve, the L6 spinal nerve, or both (Chaplan S R, Bach F W, Pogrel J W, Chung J M, Yaksh T L. *J Neurosci Methods.* 1994 July, 53(1):55-63). The experimentally-induced nerve injuries generated through SNI or SNL models typically produce symptoms of neuropathic pain including static, dynamic and/or mechanical allodynia (Costigan M, Scholz J, Woolf C J. *Annu Rev Neurosci.* 2009, 32:1-32. doi: 10.1146/annurev.neuro.051508.135531).

The rodent plantar formalin assay (formalin test) is an experimental rodent model that combines elements of nociceptive, inflammatory and neuropathic pain. The formalin test involves injection of dilute (typically 0.5% to 5%) formalin (an aqueous solution of formaldehyde) into the plantar surface of the back paw of a mouse or rat. This injection produces a characteristic pattern of voluntary nocifensive behaviors beginning within minutes of injection. A first "acute" behavioral phase involves robust biting, licking and/or flinching of the paw and is thought to be caused by nociceptive pain, which is pain that arises from direct activation of nociceptors by formalin. This first phase typically persists for 5 to 10 minutes before the behaviors subside. A subsequent phase of similar robust nocifensive behaviors follows the first phase and are typically observed between 10 and 60 minutes after formalin injection. The second phase nocifensive response may be caused by spontaneous activation of central (spinal cord) nociceptors secondary to robust peripheral activation, in some ways similar to how neuropathic pain is thought to develop, and is therefore used as a screening test to predict molecules that may have neuropathic pain relieving properties in humans (Vissers, K C et al, *Pharmacol Biochem Behav.* 2006 July; 84(3):479-86). Drugs known to reverse neuropathic pain in humans typically reduce the number of nocifensive behaviors observed in the second phase of the formalin test.

The rodent paw incision model involves inducing a surgical incision to the plantar surface of the back paw of a mouse or rat, suturing the incision closed, then testing the area proximal to the wound for changes in sensory perception, such as allodynia or hypersensitivity, at some point in time after the incision (typically 24 hours later)(Brennan T J et al. *Pain.* 1996 March, 64(3):493-501). Thermal (Hargreaves) and mechanical (von Frey) sensory testing is performed before and 24 hours after surgical incision of the plantar surface of the left back paw of laboratory rats, at a plantar area adjacent to the incision.

Hargreaves assay: Changes in the withdrawal threshold of mice upon application of a radiant heat stimulus to the plantar surface of the hind paw are determined within the context of experimentally induced inflammatory pain as previously described (Hargreaves K, Dubner R, Brown F, Flores C, Joris J. *Pain* 1988, 32:77-88).

An infrared heat stimulus is applied to the plantar surface of the back paw of a laboratory rat to test latency of voluntary withdrawal before and after plantar incision. Withdrawal latency is typically reduced in the presence of surgical inflammation, and this latency is typically reversed by treatment with clinically effective analgesics.

Von Frey assay: Changes in mechanically induced pain related behaviors are detected by first placing a rat in a transparent chamber with a wire mesh bottom. After habituation to the chamber, a "von Frey" filament is manually applied to the plantar surface of the back paw with sufficient force to cause bending of the filament. The force necessary to bend the filament is calibrated by its stiffness. Reduction in the force required to induce voluntary withdrawal will serve as a surrogate measure of injury-induced mechanical allodynia.

The invention will now be illustrated by the following non-limiting Examples.

EXAMPLES

Example 1: Preparation of Compound A-NNTA (17-Cyclopropylmethyl-3,14β-dihydroxy-4,5α-epoxy-6β-[(2'naphthyl)acetamido]morphinan)

2-Naphthoic acid (1.1 mmol, 1.1 eq), 1-hydroxybenzotriazole (1.1 mmol, 1.1 eq), and b-naltrexamine (1.0 mmol, 1 eq) were dissolved in anhydrous DMF. The solution was cooled to 0° C., at which time dicyclohexylcarbodiimide (1.2 mmol, 1.2 eq) was added. The solution was sealed under a nitrogen atmosphere and stirred at room temperature overnight (16 hrs). TLC indicated the formation of two products (N-acylated and both N- and O-acylated). The reaction mixture was filtered (to remove DCU) into water (10× initial volume of DMF) and extracted with ethyl acetate (4 times). The organic layers were combined, dried over sodium sulfate, filtered and concentrated under reduced pressure to a white foam. This was taken up in methanol and potassium carbonate (5.0 mmol, 5 eq) was added and the suspension was stirred for 1 hour at room temperature. The mixture was then concentrated under reduced pressure and the residue was dissolved in water and extracted with ethyl acetate, dried over sodium sulfate, filtered and concentrated to yield 0.32 g of desired product which was subsequently converted into the HCl salt for biological testing. Melting points were determined on a Thomas-Hoover melting point apparatus and were uncorrected. $^1$H NMR spectra and $^{13}$C NMR spectra were taken on either a Varian Inova 300 MHz or Varian Unity 300 MHz instruments. $^1$H NMR (DMSO-$d_6$): δ 0.01 (m, 2H); 0.35 (m, 2H); 0.74 (m, 1H); 1.33 (m, 4H); 1.82 (m, 2H); 2.07 (m, 1H); 2.23 (m, 1H); 2.41 (m, 1H); 2.89 (m, 2H); 3.04 (m, 1H); 3.64 (m, 1H); 4.67 (d, 1H, H-5, J=7.8 Hz); 4.81 (bs, 1H, OH-14, exc $D_2O$); 6.43 (d, 1H, H-2, J=8.1 Hz); 6.48 (d, 1H, H-1, j=7.8 Hz); 7.50 (m, 2H, Ar); 7.89 (m, 4H, Ar); 8.39 (s, 1H, Ar); 8.71 (d, 1H, amide, J=7.5 Hz); 8.94 (bs, 1H, OH-3, exc $D_2O$); mp>250° C. Anal. calcd for $C_{36}H_{35}N_5O_5$: C, 69.84; H, 6.24; N, 5.26. Found: C, 66.81; H, 6.43; N, 4.98.

Example 2: Alternate Preparation of Compound A b-Naltrexamine (400 mg, 1.16 mmol), naphthoic acid (399 mg, 2.32 mmol) and BOP (1.03 g, 2.32 mmol) were dissolved in DCM (15 mL). To this solution, DIPEA (600 mL, 3.25 mmol) was added and the mixture was stirred at room temperature for 16 hours. The solution was concentrated under reduced pressure and the residue was taken up in MeOH (15 mL), and $K_2CO_3$ was added (1.2 g). After 1 hour at room temperature, the mixture was concentrated to dryness. The final crude was purified by $SiO_2$ chromatography (eluted with EtOAc/Hexanes: 4/1) to afford the desired compound as a white solid. The target compound was recrystallized from an acetone/hexanes (1/4: v/v) mixture providing a white solid (473 mg, 82%). The title compound was then subsequently converted into the HCl salt for biological testing.

Base Form of Compound A $^1$H NMR (DMSO-d$_6$) δ: 0.12 (m, 2H); 0.47 (m, 2H); 0.86 (m, 1H); 1.27-1.63 (m, 4H); 1.85-2.03 (m, 2H); 2.09 (m, 1H); 2.22 (m, 2H); 2.37 (m, 2H); 3.01 (m, 2H); 3.75 (m, 1H); 4.76 (d, 1H, J$_{H5-H6}$=7.8 Hz); 4.92 (bs, 1H, OH-14); 6.54 (d, 1H, J$_{H1-H2}$=8.1 Hz); 6.60 (d, 1H, J$_{H2-H1}$=8.1 Hz); 7.59-7.62 (m, 2H); 7.96-8.03 (m, 4H); 8.50 (s, 1H), 8.84 (d, 1H amide, J$_{NH-H6}$=8.2 Hz); 9.05 (bs, 1H, OH-3); $^{13}$C NMR (DMSO-d$_6$) δ: 3.52, 3.65, 9.21, 22.12, 24.69, 30.06, 30.27, 43.66, 47.01, 51.63, 58.35, 61.71, 69.58, 90.64, 116.93, 118.36, 123.45, 124.08, 126.68, 127.43, 127.55 (×2), 127.77, 128.80, 131.36, 131.58, 132.08, 134.05, 140.41, 142.06, 165.52; mp=199-201° C. Anal. Calcd. for C$_{31}$H$_{32}$N$_2$O$_4$: C, 74.98; H, 6.50; N, 5.64. Found: C, 73.85; H, 6.13; N, 5.52. ESI-TOF MS m/z: 497.2930 (MH$^+$), 993.5777 (2×MH$^+$).

Salt Form of Compound A $^1$H NMR salt form (DMSO-d$_6$) δ: 0.53-0.68 (m, 4H); 1.08 (m, 1H); 1.46 (m, 2H); 1.63 (m, 1H); 1.79-1.95 (m, 2H); 2.48 (m, 2H); 2.87 (m, 1H); 3.03-3.12 (m, 2H); 3.35 (m, 2H); 3.75 (m, 1H); 3.90 (m, 1H); 4.90 (d, 1H, J$_{H5-H6}$=7.8 Hz); 6.29 (bs, 1H, OH-14); 6.65 (d, 1H, J$_{H1-H2}$=8.1 Hz); 6.74 (d, 1H, J$_{H2-H1}$=8.1 Hz); 7.59-7.62 (m, 2H); 7.97-8.03 (m, 4H); 8.52 (s, 1H), 8.90 (d, 1H amide, J$_{NH-H6}$=8.2 Hz); 9.38 (bs, 1H, OH-3); $^{13}$C NMR salt form (DMSO-d$_6$) δ: 2.57, 5.10, 5.70, 22.99, 23.80, 27.30, 29.32, 40.07, 45.56, 46.45, 51.23, 56.59, 61.56, 69.69, 89.86, 117.83, 119.23, 120.59, 124.05, 126.71, 127.49, 127.57 (×2), 127.81, 128.80, 129.66, 131.44, 132.07, 134.09, 141.28, 142.10, 165.59 mp>260° C. Anal. Calcd. for C$_{31}$H$_{33}$ClN$_2$O$_4$: C, 69.85; H, 6.24; N, 4.67. Found: C, 67.79; H, 6.44; N, 4.67. ESI-TOF MS m/z: 497.2930 (MH$^+$).

Example 3

The following illustrate representative pharmaceutical dosage forms, containing Compound A or a pharmaceutically acceptable salt thereof for therapeutic or prophylactic use in humans.

| (i) Tablet 1 | mg/tablet |
|---|---|
| Compound A= | 0.1 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound A= | 20.0 |
| Microcrystalline cellulose | 410.0 |
| Starch | 50.0 |

| (iii) Capsule | mg/capsule |
|---|---|
| Compound A = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound A = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound A = (free acid form) | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0-7.5) | q.s. |
| Water for injection | q.s. ad 1 mL |

| (vi) Aerosol | mg/can |
|---|---|
| Compound A = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

Example 4: Assays for Measuring Neuropathic Pain

Spared Nerve Injury and Spinal Nerve Ligation

Ligation of the L5 and L6 spinal nerves in rats leads to a robust pain state, characterized by tactile allodynia and mechanical hyperalgesia that can be assayed using the von Frey or Hargreaves assays (Kim, S. H. and Chung, J. M. Pain 50 (1992): 355-63). Sprague Dawley rats were housed in the animal vivarium 2 weeks prior to testing and housed on a 12 h light/dark cycle with food and water ad libitum. Under general anesthesia, the L5 and L6 spinal nerves on one side of the rat spine were tightly ligated using sterile surgical suture (Spinal Nerve Ligation, SNL). The incision site of each animal was then closed using standard surgical technique. Spared Nerve Injury: Animals were anesthetized by 2% isoflurane with 98% oxygen inhalation. A 3-4 cm skin incision was applied from the left greater trochanter to the knee joint. The muscle layers were separated to expose the sciatic nerve. The trifurcation of the sciatic nerve was identified and the common peroneal and tibial branches exposed and ligated with 5-0 silk suture, while special care was taken to avoid damage to the sural nerve. Approximately 2 mm of the nerve segments below the ligature were transected from both the branches. Several animals were tested for each group (Control Group and Compound A Treatment Group) in this study. Control group received skin incision and muscle layer separation, but no nerve injury. Animals in the Compound A treatment group received 0.3 ml of the STX formulation as a nerve block injection ipsilateral to the SNI procedure, immediately after the surgery. Animals that did not receive Compound A did not receive any other forms of treatment. The mechanical allodynia were measured at 60 minutes after administration every day (von Frey Cilia Apparatus, manufactured by Institute of Biology Bioengineering, Chinese Academy of Medical Science).

Sciatic Nerve Ligation: Rats or mice were anesthetized with sodium pentobarbital (70 mg/kg, intraperitoneal administration). The sciatic nerve at the femoral region of the right hind paw of each mouse was exposed and triply ligated tightly with silk suture of 8-0 (from NATSUME SEWA-SAKUSHO CO., LTD.) under a stereomicroscope so that only half thickness of the nerve was trapped in the ligature. A group of mice or rats thus treated was designated as a partial sciatic nerve ligation group. A group of mice or rats whose sciatic nerve was just exposed and not ligated was designated as a sham surgery group.

Figure 3:
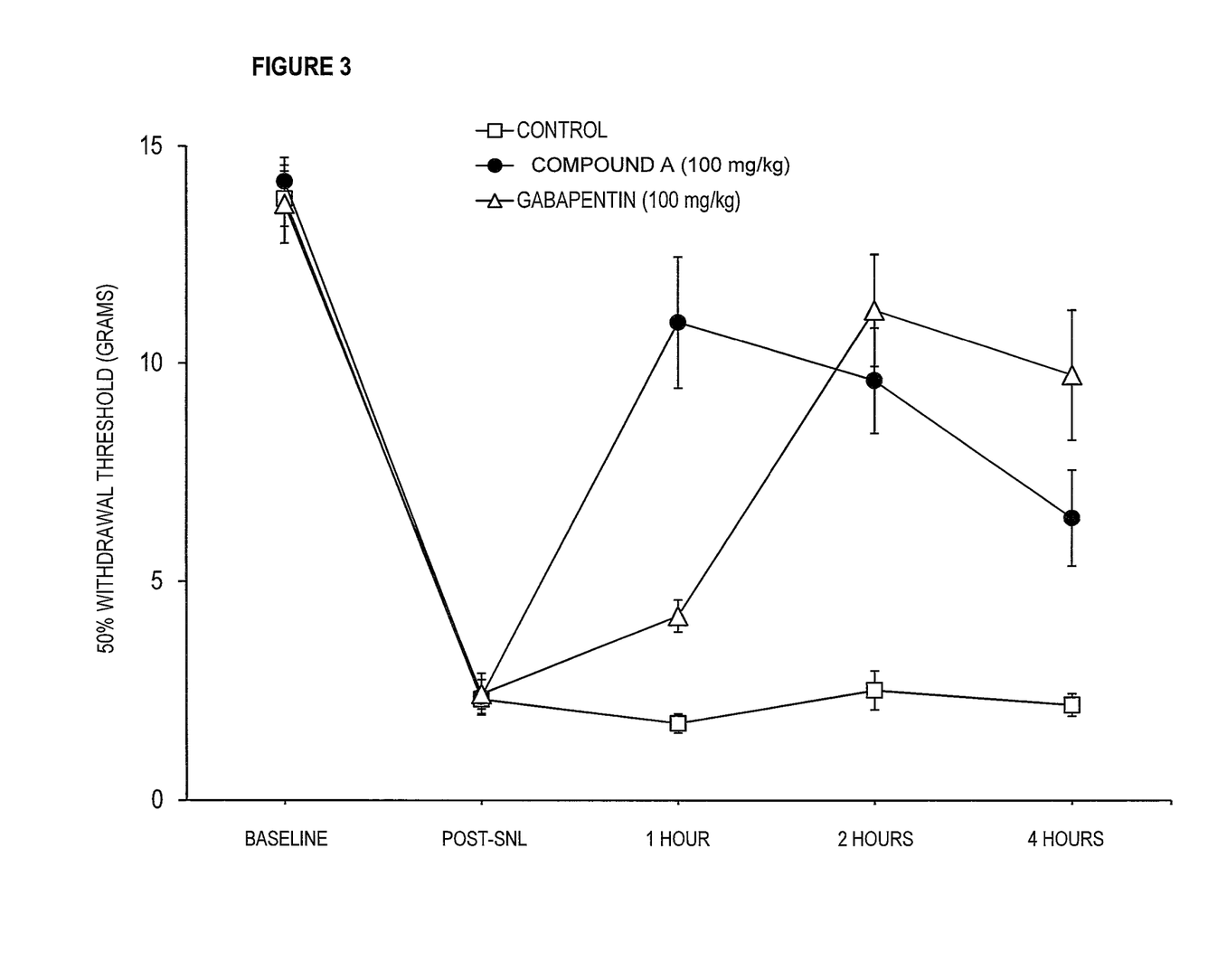
FIG. 3 is a graph showing reduced mechanical withdrawal thresholds in rats post spinal nerve ligation (post-SNL) are reversed by oral administration of Compound A or gabapentin, but not by oral vehicle (saline) administration. Circles, squares, and triangles represent mean withdrawal latency values upon administration of Compound A, saline, or gabapentin, respectively. Error bars represent Standard Error of Mean.

Baseline mechanical (von Frey) withdrawal responses were tested immediately before SNL surgery and 14 days after. Spinal Nerve Ligation led to a robust pain state, characterized by tactile allodynia and mechanical hyperalgesia observed in the 14-day post-surgical baseline values. Immediately after the 14-day post-surgical baseline responses were measured, Compound A (100 mg/kg), Gabapentin (100 mg/kg), or vehicle (control) were administered orally and voluntary withdrawal from von Frey mechanical stimuli were tested 1 hour, 2 hours and 4 hours later (FIG. 3). Orally administered Compound A was compared to the effects of oral gabapentin, which was a clinical standard of care for neuropathic pain.

Formalin Test

An injection of 0.5% formalin was made into the plantar region of a mouse right hind paw. This elicits a distinct biphasic behavioral profile characterized by the mouse licking the affected paw. Immediately following the injection the mouse licks the paw for about 10 minutes. This was phase 1 (acute) and was followed by a brief latent period where there was little behavioral activity. A more prolonged period of about 20 to 30 minutes of paw licking ensues which constitutes phase 2 (inflammatory).

Prior to the administration of the compound or vehicle each mouse underwent a 15-minute conditioning period in one of several 6" tall plexiglass observation tubes (4" diameter) that were placed in front of a mirror. Following the conditioning period, mice were treated i.p. with either vehicle, Compound A, or morphine, then returned to its home tube. One hour after treatment, formalin was injected sub-dermally (20 µl; 27 gauge needle) into the plantar surface of the right hind foot. The bevel of the needle was placed facing down toward the skin surface. Following the injection of the formalin each animal was observed for first 2 minutes of each 5 minute epoch for a total of 45 minutes. The cumulative length of licking for each 2 minute time period was measured. An animal receiving the requisite volume of vehicle was alternated with each mouse given vehicle, Compound A, or morphine. Animals were euthanized following the conclusion of the experiment.

Example 5: Models of Post-Surgical Pain

Rodent Paw Incision

Briefly, 24 hours before sensory testing, rats undergo surgery (under isoflurane anesthesia) to induce a 2 cm long incision to the left hindpaw through the skin, subcutaneous tissue to the plantar muscles using a sterile surgical scalpel. The incision site was then closed with two sterile sutures. Twenty-four hours later, the rats were injected intravenously with vehicle, 1 of 4 concentrations of morphine or 1 of 4 concentrations of Compound A (N=10 rats per treatment). The general activity of the animals was monitored following surgery along with measurement of thermal and mechanical sensitivities 24-hours after surgery as described hereafter.

Plantar incision of the hind paw of the rat produces a profound local inflammatory response characterized by pain hypersensitivity (allodynia) 24 hours after surgery in rats, in similar manner to the post-operative pain observed in humans (Brennan, T. J. et al. Pain. 1996 March; 64(3):493-501). Sprague Dawley rats were housed in the animal vivarium 2 weeks prior to testing and housed 3 per cage on a 12 h light/dark cycle with food and water ad libitum. Three days prior to testing the compound, thermal (Hargreaves) and mechanical (von Frey) sensitivity were measured using standard techniques described below. The potency of Compound A to block a plantar incision (acute tissue injury)-induced pain was then tested. Briefly, 3 h prior testing, the rats underwent surgery (under isoflurane anesthesia) to induce a 0.5 mm (L)×0.1 mm (W)×0.2 mm (D) incision to the left hindpaw through the skin, subcutaneous tissue to the plantar muscles using a sterile surgical scalpel. The rats were then injected intravenously with vehicle, ibuprofen (30 mg/kg), or Compound A (300 µg/kg) (N=10 rats per treatment). The thermal sensitivities of the animals were measured before surgery and 24 hours after surgery using the Hargreaves Thermal Withdrawal Assay (FIG. 1) (Kim, S. H. and Chung, J. M. Pain 50 (1992): 355-63).

Figure 1:
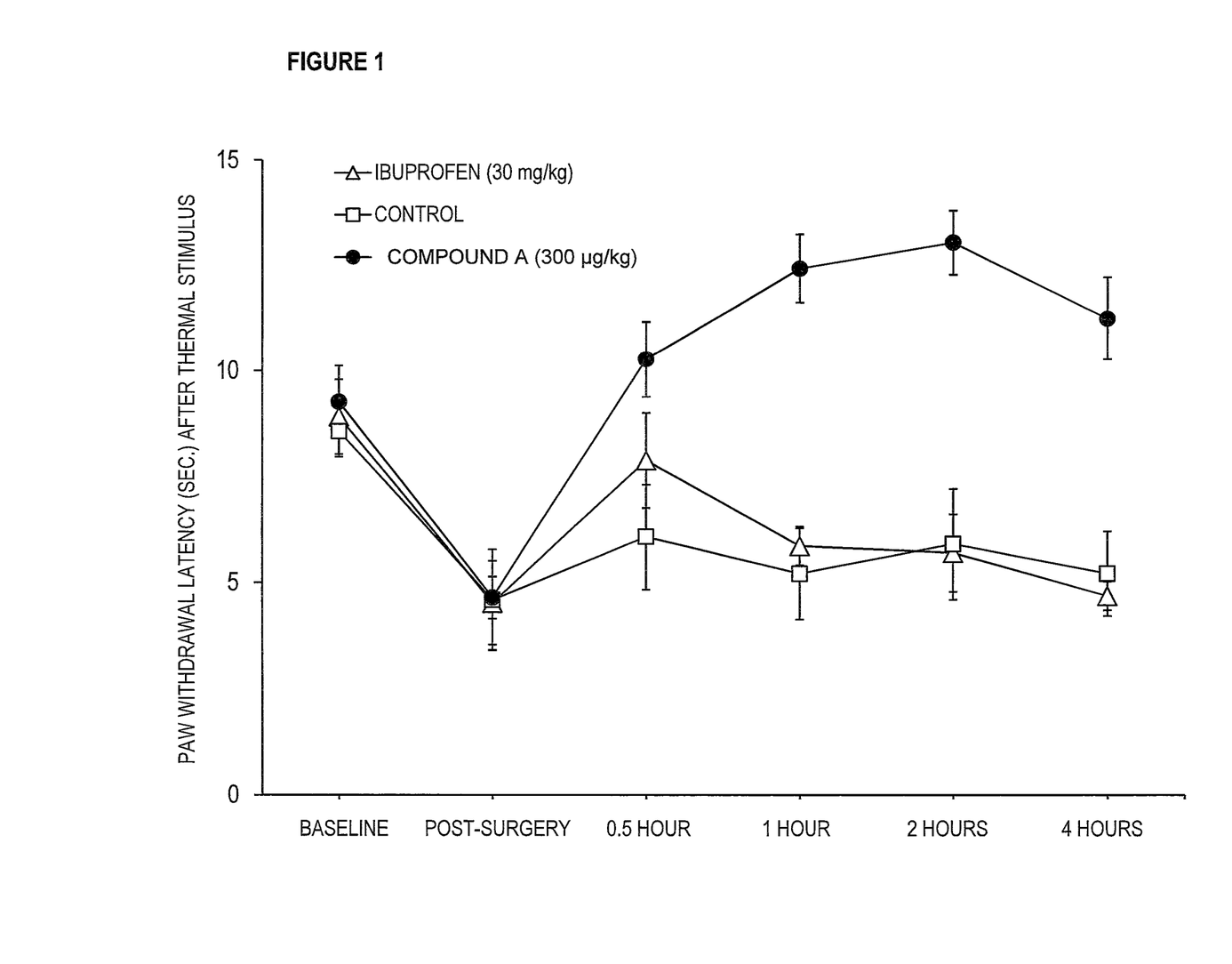
FIG. 1 is a graph showing reductions in thermal withdrawal thresholds in rats after intraplantar incision (post-surgery baseline) are reversed for four hours by intravenous Compound A (300 µg/kg) but are not reversed by intravenous saline (control) or ibuprofen (30 mg/kg). Circles, squares, and triangles represent mean withdrawal latency values upon administration of Compound A, saline, or ibuprofen, respectively. Error bars represent Standard Error of Mean.
Figure 2:
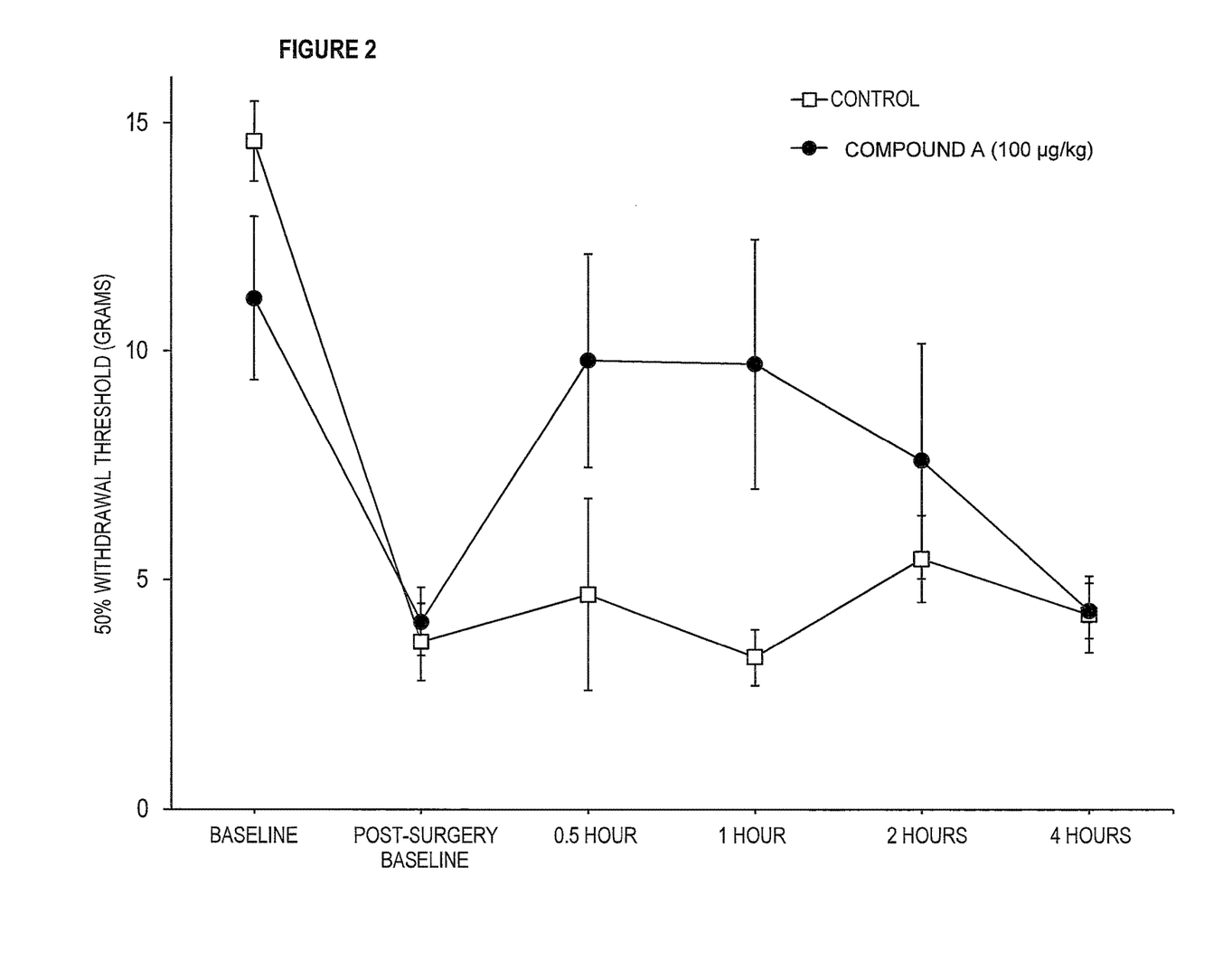
FIG. 2 is a graph showing intravenous Compound A (100 µg/kg), but not saline (control) reverses changes in mechanical withdrawal thresholds in rats after intraplantar incision (surgery). Circles and squares represent mean withdrawal latency values upon administration of Compound A or saline, respectively. Error bars represent Standard Error of Mean.

Three days prior to testing the compound, mechanical (von Frey) sensitivity were measured using standard techniques described below. The potency of Compound A to block a plantar incision (acute tissue injury)-induced pain was then tested. Briefly, 3 h prior testing, the rats underwent surgery (under isoflurane anesthesia) to induce a 0.5 mm (L)×0.1 mm (W)×0.2 mm (D) incision to the left hindpaw through the skin, subcutaneous tissue to the plantar muscles using a sterile surgical scalpel. The rats were then injected intravenously with vehicle or Compound A (100 µg/kg) (N=10 rats per treatment). The mechanical sensitivities of the animals were measured before surgery and 24 hours after surgery using the von Frey Mechanical Withdrawal Assay (FIG. 2) (Kim, S. H. and Chung, J. M. Pain 50 (1992): 355-63). Immediately after the 24 hour post-surgery baseline values were measured, intravenous compounds were administered and withdrawal responses were tested again 30 minutes (0.5 hours), 1 hour, 2 hours and 4 hours later (FIGS. 1 and 2).

Example 6: Assays for Measuring Inflammatory Pain

The antinociceptive effects of Compound A was compared to morphine and control (saline). Inflammation-mediated changes in thermal sensitivity were assessed 24 hours after paw incision using a Hargreaves thermal plantar analgesiometer (Combination Plantar/Tail Flick Analgesia Meter, IITC, CA, USA) to deliver a radiant heat source (29° C.) to the plantar hindpaw. Latency to nocifensive response, such as hindpaw flicking/licking, was recorded, with a cutoff time of 30 seconds to prevent tissue injury.

Hargreaves Assay

It was well established that thermal withdrawal latency in rats was reduced when local inflammation was present. This latency was a surrogate measure of thermal allodynia. Clinically effective analgesics typically reverse inflammation-induced changes in withdrawal latency in rodents and in humans. Voluntary withdrawal from a thermal stimulus was tested in Sprague Dawley rats of either experimental or control group by applying an infrared heat stimulus to the plantar surface of the back paw of the rats and timing the latency of the thermal pain-evoked voluntary withdrawal response as described by Hargreaves, et al., Pain. 1988; 32:77-88.

In the Hargreaves test, the mice are placed on a glass plate, and the hind leg footpads of the mice are stimulated with radiant heat (combination type analgesia meter MODEL 336 (IITC INC., U.S.A.)) every 10 minutes, and the latent time until the beginning of an escape reaction is measured. The mice with inflammatory pain are prepared by administering streptozotocin (200 mg/kg) dissolved in 0.1 N citrate buffer (pH 4.5) to caudal arteries, and the experiment is performed on the 7th day. The mice having undergone surgical inflammation are used as mice with inflammatory pain. The remaining mice are administered with 0.1 N citrate buffer at caudal arteries and used as a comparative control group (control group). The mice with inflammatory pain are divided into 4 groups, and the threshold is measured twice. The average of the values is used as a control value. Then, mice of each group are each orally administered with 300 μg/kg, 10 mg/kg or 30 mg/kg of Compound A, ibuprofen, or physiological saline (10 ml/kg), and the latent time is repeatedly measured for 60 minutes with intervals of 10 minutes. The control group is divided into two groups, and a control value is measured as described above. Then, mice of each group are each orally administered with 300 μg/kg of Compound A, 30 mg/kg ibuprofen, or physiological saline (10 ml/kg), and the latent time is measured in the same manner as described above.

Von Frey Assay

Changes in mechanically-induced pain related behaviors were tested by placing a rat of either experimental or control group into a transparent chamber with a wire mesh bottom. A plastic "von Frey" monofilament was then manually applied to the plantar surface of the back paw at different areas around the plantar surface with sufficient force to cause bending of the filament. The force necessary to bend the filament was calibrated by the stiffness of the filament with filaments of different stiffnesses was used to determine responses to different forces. Reduction in the force required to induce voluntary "nocifensive" withdrawal served as a surrogate measure of injury-induced mechanical allodynia, as described by Chaplan, et al., J. Neurosci. Meth. 53 (1994): 55-63.

Mechanical sensitivity testing was performed using previously published methods (Chaplan S R, Bach F W, Pogrel J W, Chung J M, Yaksh T L. *J Neurosci Methods* 1994; 53:55-63). The animals were placed in individual test compartments in an elevated wire mesh-bottomed platform (to provide access to the plantar surface of the hind paws). Animals were habituated to the evaluation chambers for 90 minutes in two different sessions separated by at least 1 day before starting the evaluations. The day of the evaluation, rats or mice were habituated for 60 additional minutes before the beginning of the tests. To determine mechanical thresholds, the von Frey Test was used. Rats or mice were first stimulated with a von Frey filament with a calibrated force value in the middle of the expected response range. A positive response was counted as five responses out of 10 stimuli. Each rat was then tested with higher or lower pressure filaments depending on whether they showed a positive or negative response. This was repeated until either the rat shows a response, in the case of increasing force, or until the rat does not show a response, in the case of decreasing force. The value of the lowest filament needed to induce a positive response was defined as the von Frey threshold.

INCORPORATION BY REFERENCE

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method of treating chronic pain in an animal comprising administering to the animal an amount of Compound A, (A)

or a pharmaceutically acceptable salt thereof, wherein the chronic pain is not nociceptive pain.

2. The method of claim 1, wherein the chronic pain is neuropathic pain.

3. The method of claim 2, wherein the neuropathic pain is diabetic neuropathy-induced pain, chemotherapy-induced pain, sciatica pain, carpal tunnel syndrome pain, trigeminal neuralgia pain, fibromyalgia pain, or post-herpetic neuralgia pain.

4. The method of claim 1, wherein the chronic pain is inflammatory pain.

5. The method of claim 4, wherein the inflammatory pain is somatic pain, rheumatoid arthritis pain, osteoarthritis pain, autoimmune disorder related pain, cancer pain, post-surgical pain, or post-injury pain.

6. The method of claim 1, wherein the animal is a human.

7. The method of claim 1, wherein about 100 mcg of compound A or a pharmaceutically acceptable salt thereof is administered once, twice, three, four, or five times a day.

8. The method of claim 1, wherein about 1 mg of Compound A or a pharmaceutically acceptable salt thereof is administered once, twice, three, four, or five times a day.

9. The method of claim 1, wherein about 10 mg of Compound A or a pharmaceutically acceptable salt thereof is administered once, twice, three, four, or five times a day.

10. The method of claim 1, wherein about 20 mg of Compound A or a pharmaceutically acceptable salt thereof is administered once, twice, three, four, or five times a day.

11. The method of claim 1, wherein about 100 mg of Compound A or a pharmaceutically acceptable salt thereof is administered once, twice, three, four, or five times a day.

12. The method of claim 1, wherein about 100 µg/kg of Compound A or a pharmaceutically acceptable salt thereof is administered once, twice, three, four, or five times a day.

13. The method of claim 1, wherein about 300 µg/kg of Compound A or a pharmaceutically acceptable salt thereof is administered once, twice, three, four, or five times a day.

* * * * *